(12) United States Patent
Mason

(10) Patent No.: US 9,814,688 B2
(45) Date of Patent: Nov. 14, 2017

(54) ANTIMICROBIAL COMPOSITIONS AND METHODS FOR THEIR USE

(71) Applicant: Dermcare-Vet Pty Ltd, Slacks Creek, Queensland (AU)

(72) Inventor: Kenneth Vincent Mason, Slacks Creek (AU)

(73) Assignee: Dermcare-Vet Pty Ltd, Slacks Creek (AU)

( * ) Notice: Subject to any disclaimer, the term of this patent is extended or adjusted under 35 U.S.C. 154(b) by 0 days.

(21) Appl. No.: 15/385,587

(22) Filed: Dec. 20, 2016

(65) Prior Publication Data

US 2017/0165208 A1 Jun. 15, 2017

Related U.S. Application Data

(62) Division of application No. 11/547,037, filed as application No. PCT/AU2005/000511 on Apr. 8, 2005, now Pat. No. 9,555,015.

(30) Foreign Application Priority Data

Apr. 8, 2004 (AU) ............................... 2004901924

(51) Int. Cl.
| | | |
|---|---|---|
| A61K 31/155 | (2006.01) | |
| A61K 47/20 | (2006.01) | |
| A61K 47/18 | (2017.01) | |
| A61K 47/08 | (2006.01) | |
| A61K 47/24 | (2006.01) | |

(52) U.S. Cl.
CPC ............ *A61K 31/155* (2013.01); *A61K 47/08* (2013.01); *A61K 47/18* (2013.01); *A61K 47/183* (2013.01); *A61K 47/20* (2013.01); *A61K 47/24* (2013.01)

(58) Field of Classification Search
CPC ...... A61K 31/155; A61K 47/20; A61K 47/18; A61K 47/183; A61K 47/08; A61K 47/24
See application file for complete search history.

(56) References Cited

U.S. PATENT DOCUMENTS

| | | | | |
|---|---|---|---|---|
| 4,814,334 A * | 3/1989 | Salkin | ..................... | A01N 47/44 514/256 |
| 5,422,073 A | 6/1995 | Mowrey-McKee et al. | | |
| 6,071,866 A | 6/2000 | Fujiwara et al. | | |
| 6,180,093 B1 * | 1/2001 | De | ........................ | A61K 9/0048 424/78.04 |
| 6,303,557 B1 * | 10/2001 | Colclough | ............. | A01N 47/44 510/199 |
| 9,555,015 B2 * | 1/2017 | Mason | .................. | A61K 31/155 |
| 2003/0147925 A1 | 8/2003 | Sawan et al. | | |
| 2005/0058673 A1 | 3/2005 | Scholz et al. | | |

FOREIGN PATENT DOCUMENTS

| | | |
|---|---|---|
| CA | 1150907 A | 8/1983 |
| DE | 30 07 397 A1 | 9/1981 |
| JP | 2002-524475 A | 8/2002 |
| JP | 2007-505124 A | 3/2007 |
| WO | 86/02001 A1 | 4/1986 |
| WO | 97/28805 A1 | 8/1997 |
| WO | 00/35862 A1 | 6/2000 |
| WO | 01/17357 A1 | 3/2001 |
| WO | 03/086332 A1 | 10/2003 |
| WO | 03/086348 A1 | 10/2003 |
| WO | 2005/074886 A1 | 8/2005 |

OTHER PUBLICATIONS

"Antibiotic," *Merriam-Webster Medical Dictionary*, from http://www.merriam-webster.com/medical/antibiotic, retrieved on Jun. 22, 2015.
Arch Chemicals, Inc. "Material Safety Data Sheet," *Cosmocil CQ (PCI Products)*, 1-8, (Nov. 20, 2006).
Ashworth et al., "Antimicrobial potentiation of irrigation solutions containing tris-[hydroxymethyl] aminomethane-EDTA," *Topics in Drug Therapy*, 197(11): 1513-1514 (Dec. 1, 1990).
Aursnes, "Vestibular Damage From Chlorhexidine in Guinea Pigs," *Acta Otolaryngol*, 92: 89-100 (1981).
Aursnes, "Cochlear Damage From Chlorhexidine in Guinea Pigs," *Acta Otolarryngol*, 92: 259-271 (1981).
Australian Patent Office, International Search Report in PCT/AU2005/000511 (dated May 24, 2005).
Block, "Definition of Terms," *Disinfection, Sterilization, and Preservation*, (Block ed., Lippincott Williams & Wilkins, Philadelphia, 5th Ed., 19-28 , 2001.
Broxton et al., "A study of the antibacterial activity of some polyhexamethylene biguanides towards *Escherichia coli* ATCC 8739," *Journal of Applied Bacteriology*, 54: 345-353 (1983).
Dutot et al, "Cytotoxicity of contact lens multipurpose solutions: Role of oxidative stress, mitochondrial activity and P2X7 cell death receptor activation," *European Journal of Pharmaceutical Sciences*, 33: 138-145 (2008).
Dutot et al, "Multipurpose Solutions and Contact Lens: Modulation of Cytotoxity and Apoptosis on the Ocular Surface," *Cornea*, 29(5): 541-549 (May 2010)(Abstract) Retrieved from: http://journals.lww.com/corneajrnll/Abstract/2010/05000/Multipurpose_Solutions_and_Co. . .
East et al., "Polybiguanides: synthesis and characterization of polybiguanides containing hexamethylene groups," *Polymer*, 38(15): 3973-3984 (1997).
European Patent Office, Supplemental European Search Report in EP 05729519.8, (dated Jun. 8, 2009).
Farca et al., "Potentiation of the In Vitro Activity of Some Antimicrobial Agents Against Selected Gram-Negative Bacteria by EDTA-Tromethamine," *Veterinary Research Communications*, 17: 77-84 (1993).

(Continued)

*Primary Examiner* — Sreeni Padmanabhan
*Assistant Examiner* — Jody Karol
(74) *Attorney, Agent, or Firm* — Seed IP Law Group LLP

(57) ABSTRACT

Topical and wash compositions comprising a polymeric biguanide or a bis(biguanide) compound, a chelating agent and a buffering agent and methods for using these compositions for the prevention or treatment of skin or ear tissue infections is provided.

26 Claims, 5 Drawing Sheets

(56) References Cited

OTHER PUBLICATIONS

Farca et al., "Potentiating effect of EDTA-Tris on the activity of antibiotics against resistant bacteria associated with otitis, dermatitis and cystitis," *Journal of Small Animal Practice*, 38: 243-245 (1997).
Foster et al., "The Role of Pseudomonas in Canine Ear Disease," *The Compendium*, 20(8): 909-919 (Aug. 1998).
Gotthelf, "Evaluation of the In Vitro Effect of Tris-EDTA on the Minimum Inhibitory Concentration of Enrofloxacin Against Ciprofloxacin Resistant *Pseudomonas Aeruginosa*," *Proceedings of the 19th Annual Congress of the ESVD/ECVD*, Tenerife, (Dec. 23, 2003).
Greene, "Clinical Use of Topical Buffered-EDTA Solutions in the Treatment of Gram-Negative Bacterial Infections of Dogs and Cats," *Clinical Microbiology and Infectious Diseases of the Dog and Cat*, 171 (1984).
Harper et al., "Effect of chlorhexidine/EDTA/Tris against bacterial isolates from clinical specimens,"*Microbios, 51*: 107-112 (1987).
Harvey et al., "Antimicrobial Agents, Chlorhexidine," *Ear Diseases of the Dog and Cat*, (Harvey et al., eds. Manson Publishing) 216, (2001).
Ikeda et al., "New Polymeric Biocides: Synthesis and Antibacterial Activities of Polycations with Pendant Biguanide Groups," *Antimicrobial Agents and Chemotherapy*, 26(2): 139-144 (Aug. 1984).
Izatt et al., "Thermodynamic and Kinetic Data for Macrocycle Interaction with Cations, Anions, and Neutral Molecules," *Chem. Rev., 95(7)*: 2529-2586 (1995).
Khunkitti et al., "The lethal effects of biguanides on cysts and trophozoites of *Acanthamoeba castellanii*," *Journal of Applied Bacteriology, 81*: 73-77 (1996).
Larkin et al., "Treatment of Acanthamoeba keratitis with polyhexamethylene biguanide," *Ophthalmology, 99(2)*: 185-191 (Feb. 1992) (Abstract).
Merchant et al., "Ototoxicity Assessment of a Chlorhexidine Otic Preparation in Dogs," *Progress in Veterinary Neurology, 4(3)*: 72-75.
Merchant, "Ototoxicity," *Veterinary Clinics of North America: Small Animal Practice, 24(5)*: 971-980 (Sep. 1994).
Messick et al., "In-vitro activity of polyhexamethylene biguanide (PHMB) against fungal isolates associated with infective keratitis," *J. Antimicrob. Chemother. 44*: 297-298 (1999).
Neer et al., "Otitis Media," *The Compendium on Continuing Education, 4(5)*: 410-417 (May 1982).
Paterson, "New Concepts in Ear Cleaning TrizEDTA (EDTA tris)," *DermaPet Articles of Interest*, Retrieved from http://www.dermapet.com/articles/new_concepts.html (Nov. 11, 2003).
Pearman et al., "Comparison of the Efficacy of 'Trisdine' and Kanamycin-Colistin Bladder Instillations in Reducing Bacteriuria during Intermittent Catheterisation of Patients with Acute Spinal Cord Trauma," *British Journal of Urology, 62*: 140-144 (1988).
Quinn et al., "Antimicrobial Agents," *Clinical Veterinary Microbiology*, (Quinn et al., eds., Mosby, Edinburgh) 95-117 (1994).
Rohn et al., "Ototoxicity of Topical Agents," *Otolaryngologic Clinics of North America, 26(5)*: 747-758 (Oct. 1993).
Schwarb et al., "Microbiological Quality of Topical Drug Formulations: Efficacy of Antimicrobial Preservation against *Paecilomyces lilacinus*," *Dermatology, 203*: 248-255 (2001).
Sentell et al., "Comparison of Preservative Uptake and Release Profiles of PHMP from Soft Contact Lens Care Products by Silicone Hydrogel Contact Lenses," *Invest. Ophthalmol. Vis. Sci., 45: E-Abstract* 1573 (2004) (2 pages) (Abstract).
Sparks et al., "Antimicrobial Effect of Combinations of EDTA-TRIS and Amikacin or Neomycin on the Microorganisms Associated with Otitis Externa in Dogs," *Veterinary Research Communications, 18*: 241-249 (1994).
Willoughby, "Chlorhexidine and Ototoxicity in Cats," *The Veterinary Record*, 547 (May 20, 1989).
Wooley et al., "Action of EDTA-TRIS and Antimicrobial Agent Combinations on Selected Pathogenic Bacteria," *Veterinary Microbiology, 8*: 271-280 (1983).
Wooley et al., "In Vitro action of combinations of antimicrobial agents and EDTA-tromethamine on *Escherichia coli*," *Am. J. Vet. Res., 44(6)*: 1154-1158 (Jun. 1983).
Wright et al., "In Vitro Cytotoxicity of Soft Contact Lens Care Products with and without PHMB," *Investigative Ophthalmology & Visual Science, 45: E-Abstract 1534* (2004).

\* cited by examiner

ANTIMICROBIAL COMPOSITIONS AND METHODS FOR THEIR USE

This invention relates to the treatment or prevention of skin and ear tissue infections in mammals involving application of a wash composition comprising a polymeric biguanide or a bis(biguanide) compound, a chelating agent and a buffering agent. The invention further relates to compositions useful in such treatment or prevention.

Treatment of infections of the skin and epithelial lined body cavities and particularly the external ear, can be very difficult as these areas attract antimicrobial resistant microorganisms in humans and warm blooded animals. The antimicrobial resistance may be developed as a consequence of repeated exposure to antimicrobial drugs during treatment of recurrent infections and subsequent selection of resistant strains, or may be a result of invasion by a micro-organism which has inherent antimicrobial resistance.

The commonly encountered micro-organisms that infect the ears of mammals include the bacteria *Staphylococcus* spp. Enterobacteriacae such as *Escherichia coli, Klebsiella* spp, *Proteus mirabilis, Proteus vulgaris* and Pseudomonads such as *Pseudomonas aeruginosa*. These micro-organisms are known to thrive in cavities, such as ear canals, and sometimes even benefit from antimicrobial treatment, possibly by removal of other susceptible micro-organisms competing for the same environment. An example of such a phenomenon is the dramatic overgrowth of *Malassezia* after reduction in *Pseudomonas* numbers (Foster, DeBoer 1998).

Ear infections are often difficult to treat as inflammatory cells, biological proteins, enzymes, DNA and other chemicals and biological compounds in a purulent exudate around an infection in the ear decrease or inactivate the antimicrobial and biocidal action of drugs prescribed for treatment of the infection. Many drugs that are prescribed to treat infections are neuro-toxic and thus ototoxic (Rohn et. al. 1993).

There is a need for a simple and effective treatment for ear infections that is rapid and active at low levels, below ototoxic levels. There is also a need for treatments that have a broad action in reversing the resistance spectrum of an infection to antimicrobial drugs.

A combination of a chelating agent, ethylenediaminetetraacetic acid (EDTA), and a buffering agent, tris(hydroxymethyl)aminomethane (Tris), has previously been used as an ear wash in dogs. It is known that this combination has some antimicrobial activity, but the primary advantage of the Tris-EDTA combination is that it improves the susceptibility of micro-organisms, particularly micro-organisms with antimicrobial resistance, to the effects of antibiotics (Ashworth and Nelson, 1990; Green, 1984; Neer, 1982; Foster and DeBoer, 1998; Farcia, 1993; Farcia, 1997; Gotthelf, 2003). However, in the order of 10 to 15 minutes exposure of Tris-EDTA to the ear canal may be required (Paterson, 2003). Farcia (1997) found that using a non-proprietary Tris-EDTA solution was effective after 10 minutes. Some in vitro models require hours for these beneficial effects (Woolley et. al., 1983a, 1983b) although Gotthelf (2003) found an in vitro lowering of the minimum inhibitory concentration (MIC) effect of Tris-EDTA could occur at 5 and 30 minutes. Such prolonged times may be difficult in domestic animals such as dogs and cats that shake their heads to remove liquid from their ears upon administration of the ear wash.

Current Tris-EDTA flush solutions have a minimal effect on Gram positive organisms and no effect on yeasts like *Candida* and *Malassezia* due to differences in cell walls (Foster and DeBoer, 1998; Sparkes et. al., 1994). Patterson (2003) advises "In fact prolonged use of EDTA-tris like many water based [ear] cleaners can predispose to *Malassezia* infection".

WO 03/086332 has described the use of a preserved Tris-EDTA formulation as a wash solution. In this case, the chosen preservative was non-ionic and selected to allow conformance with USP preservative efficacy testing. This solution could be used alone as an antiseptic wash or may be used as a carrier for an antibiotic.

Tris is not known to have any biological activity, however, it is known that EDTA chelates calcium and magnesium ions in water. It is speculated that EDTA is able to bind calcium and magnesium ions in bacterial cell walls, weakening the cell walls and thereby improving the effects of subsequent treatment with antibiotics.

Biguanide compounds are known antiseptics and have been used as topical antiseptics, in contact lens solutions and as disinfectants for wastewater and its containers. Biguanides include bis(biguanides) such as chlorhexidine and alexidine and polymeric biguanides such as polyhexamethylene biguanide (PHMB) and others as described in the literature (East et. al., 1997; Ikeda et. al., 1984).

The bis(biguanide) chlorhexidine has been used in many antiseptic applications. Ototoxicity has occasionally been reported when chlorhexidine was used as a presurgical antiseptic in and around the ear in man and animals. However, there are conflicting reports of the ototoxicity of chlorhexidine (Willoughby K., 1989; Merchant S. R., 1994; Aursnes, J., 1981a and 1981b). Some studies have shown that compositions containing chlorhexidine are ototoxic especially in concentrations as high as 2%, this is particularly so when the tympanic membrane has been ruptured (Harvey et. al., 2001; Merchant, 1994). Other studies have shown no ototoxic effects when 0.2% chlorhexidine was placed in the external ear of dogs with ruptured tympanic membranes (Merchant et. al., 1992). The combination of chlorhexidine with ethanol or quaternary ammonium compounds such as centrimide, enhances ototoxicity (Harvey et. al., 2001). Great care must be taken with administration of chlorhexidine to the ear to ensure that the tympanic membrane is intact, the concentration is below ototoxic amounts and that no additives are present that may enhance its ototoxic effect.

Chlorhexidine (0.01%) has also been used in combination with Tris-EDTA as a bladder instillation in patients with spinal cord trauma requiring intermittent catheterisation (Harper, 1987; Pearman, 1988). However, 0.02% chlorhexidine compositions were found to cause chemical cystitis resulting in haematuria (Pearman, 1988).

Advantageously, the present inventor has found that a combination of a biguanide compound with a buffering agent and a chelating agent may provide a rapid and effective treatment for ear infections and infections of other tissues such as skin and may improve the susceptibility of micro-organisms to the effects of antibiotics.

According to an aspect of the present invention there is provided a method of inhibiting, treating or preventing infections of the skin in a mammal, comprising topical administration of an effective amount of a composition comprising:
 (i) a chelating agent,
 (ii) a buffering agent, and
 (iii) at least one bis(biguanide) or polymeric biguanide or a mixture thereof, or pharmaceutically acceptable salts thereof,
to the skin of the mammal.

According to another aspect of the invention, there is provided a pharmaceutical or veterinary composition comprising:
(i) a chelating agent,
(ii) a buffering agent, and
(iii) at least one bis(biguanide) or polymeric biguanide or a mixture thereof, or pharmaceutically acceptable salts thereof;
with the proviso that component (iii) is not chlorhexidine.

According to a further aspect, there is provided a use of
(i) a chelating agent,
(ii) a buffering agent, and
(iii) at least one bis(biguanide) or polymeric biguanide or a mixture thereof, or pharmaceutically acceptable salts thereof,
in the manufacture of a medicament for the treatment or prophylaxis of infections of the skin of a mammal.

The invention is particularly useful for inhibiting, treating or preventing infections of the external ear.

Suitable mammals include any mammal prone to skin infections such as ear infections, for example humans, domestic animals such as pets and agriculturally useful animals, such as sheep, cattle, pigs and horses. Particularly preferred mammals are humans and pets, such as cats and dogs, especially preferred mammals are dogs, especially long-haired, pendulous-eared breeds of dog.

As used herein, the term "external ear" refers to the pinna or auricle and the auditory canal or meatus of the ear.

The method and composition of the invention are particularly useful for inhibiting or treating infections caused by yeasts, Gram positive and/or Gram negative bacteria, especially those bacteria that have at least some resistance to the effects of antibiotics. The method and composition is particularly useful for treating or inhibiting infections caused by *Staphylococcus* spp such as *Staphylococcus aureus, Staphylococcus intermedius*, Enterobacteriacae such as *Escherichia coli, Klebsiella* spp, *Proteus* spp such as *Proteus mirabilis* and Pseudomonads such as *Pseudomonas aeruginosa, Streptococcus* spp. and yeasts such as *Malassezia pachydermatis* and *Candida albicans* and fungi such as *Aspergillus* spp. Preferably, the methods and compositions are used for treating or inhibiting infections caused by *Pseudomonas aeruginosa, Staphylococcus intermedius* and *Malassezia pachydermatis*.

A biguanide compound comprises a group of the formula:

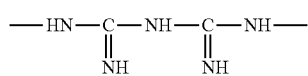

(I)

or a salt or tautomer thereof.

A bis(biguanide) comprises two groups of formula (I) or salts thereof linked by a divalent bridging group and a polymeric biguanide comprises 3 or more groups of formula (I) or salts thereof, each linked by a divalent bridging group.

Preferred bis(biguanides) are those having the following formula:

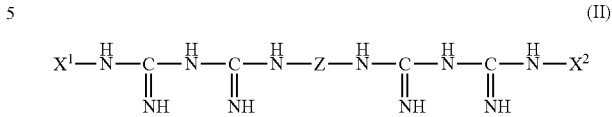

(II)

or a tautomer thereof, wherein Z is a divalent bridging group and $X^1$ and $X^2$ are independently selected from optionally substituted alkyl, optionally substituted aryl, optionally substituted cycloalkyl, optionally substituted heterocyclyl or optionally substituted heteroaryl or a pharmaceutically or veterinarily acceptable salt thereof. The above bis(biguanide) compounds and methods for their preparation are described, for example, in U.S. Pat. Nos. 4,670,592 and 4,952,704. Preferred bis(biguanides) include chlorhexidine (commercially available from various sources such as Degussa AG of Dusseldorf, Germany), where $X^1$ and $X^2$ are both 4-chlorophenyl and Z is —$(CH_2)_6$— and alexidine (commercially available from Ravensberg GmbH Chemische Fabrik, Konstanz, Germany), where $X^1$ and $X^2$ are both 3-ethylhexane and Z is —$(CH_2)_6$—.

In a preferred embodiment the biguanide is a polymeric biguanide such as those described by East et. al., 1997 in which the biguanide appears in the polymer backbone. Especially preferred polymeric biguanides having the following formula:

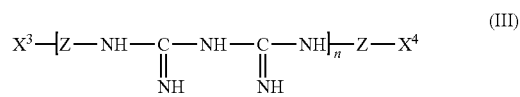

(III)

or a tautomer thereof, wherein Z is absent or an organic divalent bridging group and each Z may be the same or different throughout the polymer; n is at least 3, preferably 5 to 20 and $X^3$ and $X^4$ are independently selected from —$NH_2$, —NH—C(=NH)—NH—CN, optionally substituted alkyl, optionally substituted cycloalkyl, optionally substituted aryl, optionally substituted heterocyclyl and optionally substituted heteroaryl; or a pharmaceutically or veterinarily acceptable salt thereof. Preferably, the molecular weight of the polymeric compound is at least 1,000 amu, more preferably between 1,000 amu and 50,000 amu. In a single composition, n may vary providing a mixture of polymeric biguanides. In some embodiments, the polymeric biguanides have a mean molecular weight in the region of 2,900 to 15,000, especially 3,000 to 8,000, and particularly 3,200 to 5,000, especially 3,500 to 4,500.

The above polymeric biguanide compounds and methods for their preparation are described in, for example, U.S. Pat. No. 3,428,576 and East et. al., 1997.

Preferred polymeric biguanides in which the biguanide appears in the backbone of the polymer for use in the invention are polymeric hexamethylene biguanides such as polyhexanide or PHMB (commercially available as Vantocil, Baquacil, Arlagard, Lonzabac BG or Cosmocil) of the following formula:

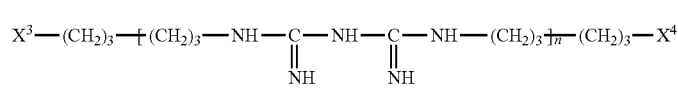

(IV)

or a tautomer thereof, wherein n is an integer from 3 to 500 and $X^3$ and $X^4$ are independently selected from —$NH_2$, —NH—C(=NH)—NH—CN, optionally substituted alkyl, optionally substituted cycloalkyl, optionally substituted aryl, optionally substituted heterocyclyl and optionally substituted heteroaryl or a pharmaceutically or veterinarily acceptable salt thereof. Preferably n has an average value of 3 to 15, more preferably 3 to 12. Most preferred are polymeric hexamethylene biguanides, commercially available, for example, as the hydrochloride salt, from Avecia (Wilmington, Del., USA) under the trademark Cosmocil CQ™.

In another embodiment of the invention, the polymeric biguanides are fractionated polymeric biguanides where the lower molecular weight proportion of polymer is removed. In particular, polymeric biguanide compositions in which the fraction of oligomers having a value of n≤5 is less than 2 wt %, preferably less than 0.5 wt % and most preferably is less than 0.1 wt % of the polymeric biguanides in the composition.

Other preferred polymeric biguanides are those with pendant biguanide groups having the formula:

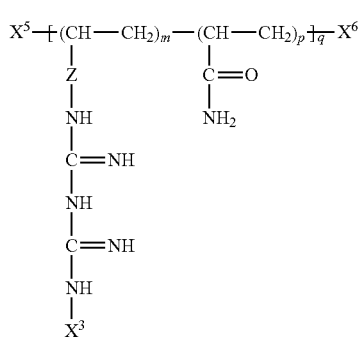

(V)

or a tautomer thereof, wherein $X^3$ is defined for formula III above, $X^5$ and $X^6$ are independently selected from H or $X^3$, Z is absent or is a divalent bridging group, m is an integer from 1 to 10, p is 0 or an integer from 1 to 10 and q is an integer from 1 to 1000; or a pharmaceutically or veterinarily acceptable salt thereof.

Preferred polymeric biguanides having pendant biguanide groups are those described by Ikeda et. al., 1984 in which $X^5$ and $X^6$ are hydrogen, Z is —C(O)—O—$CH_2CH_2$—$C_6H_4$—, $X^3$ is phenyl or optionally substituted phenyl, especially 4-chlorophenyl or 3,4-dichlorophenyl, m is an integer from 1 to 10, p is 0, q is an integer from 1 to 500 (homopolymer) or where m is 1 to 10, p is 1 to 10 and q is 1 to 500 (co-polymer with acrylamide).

The polymeric biguanides having pendant biguanide groups and methods for their preparation are described in Ikeda et. al., 1984.

As used herein, the term "alkyl" refers to monovalent, straight chain or branched hydrocarbon groups, having 1 to 10 carbon atoms as appropriate. For example, suitable alkyl groups include, but are not limited to, methyl, ethyl, propyl, isopropyl, n-butyl, sec butyl, tert-butyl, pentyl, 2-methylpentyl, 3-methylpentyl, n-hexyl, 2-, 3- or 4-methylhexyl, 2-, 3- or 4-ethylhexyl, heptyl, octyl, nonyl and decyl.

As used herein, the term "cycloalkyl", refers to cyclic hydrocarbon groups. Suitable cycloalkyl groups include, but are not limited to, cyclopropyl, cyclobutyl, cyclopentyl and cyclohexyl.

The term "aryl" as used herein, refers to $C_6$-$C_{10}$ aromatic hydrocarbon groups such as phenyl and naphthyl.

The term "heterocyclyl" or "heterocyclic", as used herein, refers to monocyclic, polycyclic, fused or conjugated cyclic hydrocarbon residues, preferably $C_{3-6}$, wherein one or more carbon atoms (and where appropriate, hydrogen atoms attached thereto) are replaced by a heteroatom so as to provide a non-aromatic residue. Suitable heteroatoms include, O, N and S. Where two or more carbon atoms are replaced, this may be by two or more of the same heteroatom or by different heteroatoms. Suitable examples of heterocyclic groups may include, but are not limited to, pyrrolidinyl, pyrrolinyl, piperidyl, piperazinyl, morpholino, indolinyl, imidazolidinyl, pyrazolidinyl, thiomorpholino, dioxanyl, tetrahydrofuranyl, tetrahydropyranyl, tetrahydropyrrolyl.

The term "heteroaryl" or "heteroaromatic", as used herein, represents a stable monocyclic or bicyclic ring of up to 6 atoms in each ring, wherein at least one ring is aromatic and contains from 1 to 4 heteroatoms selected from the group consisting of O, N and S. Heteroaryl groups within the scope of this definition include, but are not limited to, acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline.

Alkyl, cycloalkyl, heterocyclyl, heteroaryl and aryl groups of the invention may be optionally substituted with 1 to 5 groups selected from OH, $OC_{1-6}$alkyl, Cl, Br, F, I, $NH_2$, $NH(C_{1-6}alkyl)$, $N(C_{1-6}alkyl)_2$, SH, $SC_{1-6}$alkyl, $CO_2H$, $CO_2C_{1-6}$alkyl, $CONH_2$, $CONH(C_{1-6}alkyl)$ or $CON(C_{1-6}alkyl)_2$.

As used herein, the term "divalent bridging group" refers to a radical that has a valence of two and is able to bind with two other groups. Examples of suitable divalent bridging groups include, but are not limited to, —$(CH_2)_t$— where t is an integer from 1 to 10, —O—, —S—, a divalent saturated or aromatic carbocyclic ring or a heterocyclic or heteroaromatic ring or a combination of such divalent and/or cyclic moieties. For example a saturated $C_6$ cyclic group would include —$C_6H_{10}$—, a $C_6$ aromatic group would include —$C_6H_4$—, a $C_6$ heterocyclic group would include

and a $C_6$ heteroaromatic would include

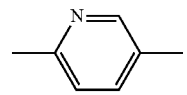

Other divalent bridging groups include alkylene groups (—$CH_2$—)$_t$ in which one or more carbon atoms have been replaced by NH, S, O,

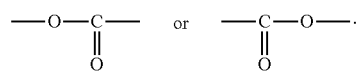

In a preferred embodiment the divalent bridging group is —(CH$_2$)$_t$— where t is an integer from 1 to 10, especially 1 to 6, more especially 6.

As used herein, the term "tautomer" refers to isomeric forms of a compound which have migration of a hydrogen atom accompanied by movement of adjacent double bonds. For example, Formula (I) may tautomerise to provide different isomers according to the following equation:

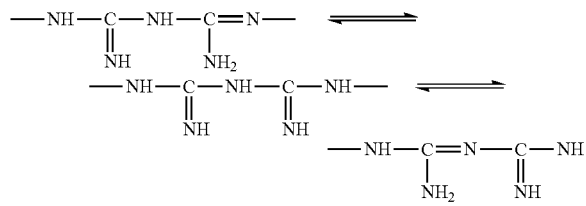

When used herein, the terms Antiseptic, Antimicrobial, Preservative, Antibiotic, Disinfectant and Antibacterial shall have the meanings as prescribed in Block S. (2001) which is the internationally accepted text on the subject.

Thus the term "Antiseptic" as used herein refers to a substance that prevents or arrests the growth or action of microorganisms either by inhibiting their activity or by destroying them. The term is used especially for preparations applied topically to living tissue. Thus "Skin (including ear) Antiseptic" refers to a safe, non-irritating, liquid, antimicrobial preparation that prevents overt skin/ear infection.

The term "Preservation" as used herein refers to the process by which chemical or physical agents prevent biological deterioration of substances. The term "Preservative" as used herein refers to an agent that inhibits the growth of microorganisms capable of causing biological deterioration of a substance(s)/material(s).

The term "Antimicrobial" as used herein refers to the killing or suppression of the growth of microorganisms.

The term "Antibiotic" as used herein refers to an organic chemical substance produced by a microbial organism, that has the capacity in dilute solutions to destroy or inhibit the growth of bacteria and other microorganisms.

The term "Antibacterial" as used herein is the same as bacteriocide and refers to an agent that kills bacteria and is applied to living tissue.

The term "Disinfectant" as used herein refers to an agent that frees from infection, usually a chemical agent but sometimes a physical one. It refers to substances applied to inanimate objects.

Under the conditions of use, for example, at the prepared and in use pH of the compositions, the biguanide compounds are in ionic form. Suitable pharmaceutically or veterinarily acceptable salts of the ions include, but are not limited to, salts of pharmaceutically acceptable inorganic acids such as hydrochloric, sulphuric, phosphoric, phosphonic, phosphanilate, nitric, carbonic, boric, sulfamic, sulfonic and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, (4-aminophenyl)phosphonic, phenylphosphonic, salicylic, sulphanilic, aspartic, glutamic, edetic, stearic, palmitic, oleic, lauric, pantothenic, tannic, ascorbic and valeric acids. Preferred salts include salts of hydrochloric, boric, sulfonic, acetic, lactic, phosphanilate, gluconic, citric and tartaric acids.

Preferably the chelating agent is selected from any compound that is able to sequester monovalent or polyvalent metal ions such as sodium, lithium, rubidium, cesium, calcium, magnesium, barium, cerium, cobalt, copper, iron, manganese, nickel, strontium or zinc, and is pharmaceutically or veterinarily acceptable. Suitable chelating agents include, but are not limited to amino carboxylic acids and salts thereof such as ethylene diamine tetraacetic acid (EDTA), nitrilotriacetic acid, nitrilotripropionic acid, diethylenetriamine pentaacetic acid, 2-hydroxyethyl-ethylenediamine-triacetic acid, 1,6-diamino-hexamethylene-tetraacetic acid, 1,2-diamino-cyclohexane tetraacetic acid, O,O'-bis(2-aminoethyl)-ethyleneglycol-tetraacetic acid, 1,3-diaminopropane-tetraacetic acid, N,N-bis(2-hydroxybenzyl)ethylenediamine-N,N-diacetic acid, ethylenediamine-N,N'-diacetic acid, ethylenediamine-N,N'-dipropionic acid, triethylenetetraamine hexaacetic acid, 7,19,30-trioxa-1,4,10,13,16,22,27,33-octaazabicyclo[11,11,11]pentatriacontane (O-bis-tren), ethylenediamine-N,N'-bis(methylenephosphonic acid), iminodiacetic acid, N,N-bis(2-hydroxyethyl)glycine (DHEG), 1,3-diamino-2-hydroxypropane-tetraacetic acid, 1,2-diaminopropane-tetraacetic acid, ethylenediaminetetrakis(methylenephosphonic acid), N-(2-hydroxyethyl) iminodiacetic acid and triethylenetetramine-hexaacetic acid, deferoxamine, dimercaprol, citrate and its salts such as zinc citrate, penicillamine and its salts and biphosphonates such as editronate or macrocyclic polyethers, such as those described in the literature (Izatt R. M. et. al., 1995). Especially preferred chelating agents are pharmaceutically and veterinarily acceptable salts and mixed salts of EDTA such as disodium, trisodium, tetrasodium, dipotassium, tripotassium, lithium, dilithium, ammonium, diammonium, calcium and calcium-disodium, most preferably disodium or tetrasodium salts of EDTA, especially disodium EDTA.

Buffering agents suitable for use in the invention are those that are pharmaceutically or veterinarily acceptable. Preferred buffering agents include, but are not limited to, amines such as triethylamine, triethylenetetramine tetraethylethylenediamine, tetramethylenediamine and N,N'-diethyl-N,N'-bis(sulfopropyl)ethylenediamine (DESPEN); piperazines such as N,N'-diethylpiperazine and piperazine-N,N'-bis(alkylsulfonic acids); histadines, imidazoles, morpholines such as the (N-morpholino)alkylsulfonic acids, for example, 2-morpholineethanesulfonic acid and 4-morpholinepropane sulfonic acid, aminoalcohols such as 2-aminoethanol and 2-amino-2-methyl-1-propanol (AMP) and triethanolamine, and the aminopolyols, boric acid, bicarbonate salts such as sodium bicarbonate, sodium chloride, meglumine, phosphate buffers, citrate buffers and salts thereof. Particularly preferred buffers are aminopolyols such as tris(hydroxymethyl)aminomethane (also known as Tris, THAM, tromethamine and trometamol), 2-amino-2-methyl-1,3-propanediol (also known as AMPD), 2,2-bis(hydroxymethyl)-2,2',2"-nitrilotriethanol (also known as BIS-TRIS) and 1,3-bis(tris[hydroxymethyl]methylamino)propane (also known as BIS-TRIS propane and BTP), triethanolamine and salts thereof and mixtures thereof. An especially preferred buffer is Tris. In preferred embodiments, the composition should be buffered between pH 3 to 9, most preferably pH 5 to 8. In some embodiments, the pH is about pH 8. In other embodiments, the pH is between 6 and 7.

In preferred embodiments, the bis or polymeric biguanide is present in a concentration of 0.0001% (1 ppm) to 10% w/w of the composition, preferably 0.001 to 5% w/w, most preferably 0.001 to 2% w/w, especially between about 0.02% and 0.2% w/w. In some embodiments, including, but not limited to, use of chlorhexidine, the concentration of the bis or polymeric biguanide is in the range of greater than 0.02% and 0.5% w/w, especially 0.05 to 0.2% w/w or 0.1 to 0.2% w/w.

The amount of chelating agent present will depend on the nature of the chelating agent and its effectiveness in chelating ions from bacterial cell walls. The chelating agent will generally be present at a concentration of 0.0001% (1 ppm) to 5% w/w of the composition, preferably 0.05 to 2% w/w, most preferably 0.1 to 0.2% w/w, especially about 0.12% w/w.

The amount of buffering agent will depend on the nature of the buffering agent and the pH required for the composition. In some embodiments, the buffering agent will generally be present at a concentration of 0.0001% (1 ppm) to 5% w/w of the composition, preferably 0.01 to 2% w/w, most preferably 0.1 to 1% w/w, especially about 0.6% w/w. In other embodiments the buffering agent will be present at a concentration in the range of 0.0001 moles per liter to 5 moles per liter, preferably 0.001 to 2 moles per liter, most preferably 0.01 to 0.1 moles per liter, especially about 0.05 moles per liter.

In one embodiment, the composition may further include an additive which enhances the antimicrobial activity of the composition. Such additives include propylene glycol, glycerin, polypropylene glycol(s), polyethylene glycol(s), an antibiotic or a mixture of propylene glycol and/or polypropylene glycol(s) and/or polyethylene glycol(s) and/or glycerin and/or an antibiotic.

In another embodiment, the method of the invention includes a further subsequent step in which an antibiotic is administered to the mammal. Suitable antibiotics include, but are not limited to, fluoroquinolones such as ciprofloxacin, norfloxacin, ofloxacin, enoxacin, perfloxacin, fleroxacin, enrofloxacin, marbofloxacin, sarafloxacin, orbifloxacin, danofloxacin; aminoglycosides such as streptomycin, netilmicin, kanamycin, neomycin, tobramycin, amikacin, sisomicin, ribostamycin, dibekacin, framycetin, gentamycin, penicillins and aminopenicillins such as penicillin, ampicillin, amoxicillin, nafcillin, oxacillin and ticarcillin, cephalosporins such as ceftriaxone, cephalexin, cefadroxil and ceftiofur, β-lactams such as clavulanic acid which may be used in conjunction with penicillins or aminopenicillins, macrolides such as clarythromycin and erythromycin and other antibiotics such as dactinomycin, clindamycin, naladixic acid, chloramphenicol, rifamopin, clofazimine, spectinomycin, polymyxin B, colistin, minocycline, vancomycin, hygromycin B or C, fusidic acid, trimethoprim and cefotaxim.

Topical administration according to the invention may be by means of a liquid or vaporised composition. Suitable liquid compositions include lotions, ointments and gels and include aqueous solutions. Preferred compositions are aqueous compositions. Suitable vaporised compositions include sprays and aerosols. Preferably the topical administration is administration of a liquid composition by lavage or by administration of ear drops or by spray, such as that delivered by a trigger spray bottle. Other suitable means of application are known in the art, for example, a moistened gauze, swab, cotton, foam, sponge or cloth. It is particularly preferred that the liquid composition is applied by lavage. Of particular benefit is the physical flush effect that disrupts encrusted purulent and waxy accumulated material away from the ear lining, breaking it up and allowing penetration of other medications and flushing it from the ear canal. Such a liquid flushing composition may be applied using a flush applicator. Suitable carriers for use in topical compositions include, but are not limited to, mineral oil, propylene glycol, polyethylene glycols, polyoxyethylene, polyoxypropylene, emulsifying wax, sorbitan monostearate, polysorbate 20, polysorbate 60, cetyl esters, wax, cetearyl alcohol, 2-octyldodecanol, benzyl alcohol, ethanol, N-methyl pyrrolidone and water. An especially preferred carrier is water.

As used herein, the term "effective amount" relates to an amount of the composition which, when administered according to a desired dosing regimen, provides the desired therapeutic activity or infection prevention. Dosing may occur at intervals of minutes, hours, days, weeks, months or years. An inhibiting effective amount is an amount of the composition, which when administered according to the desired dosage regimen, is sufficient to prevent the multiplication of microbes responsible for infection. A therapeutic effective amount or treatment effective amount is an amount of the composition, which when administered according to a desired dosage regimen, is sufficient to at least partially attain the desired therapeutic effect, or delay the onset of, or inhibit the progression of, halt, partially or fully the onset or progression of the infection or is able to reverse or partially reverse the antibiotic sensitivity of the organisms including lowering the minimum inhibitory concentration (MIC) or inducing a synergistic interaction. A preventative effective amount of the composition, which when administered according to a desired dosage regimen, is sufficient to at least partially prevent or delay the onset of the infection.

Suitable dosage amounts and dosing regimens can be determined by the attending physician or veterinarian and may depend on the severity of the infection as well as the general age, health and weight of the subject being treated.

While in its simplest form the composition of the invention may be an aqueous composition consisting of a polymeric biguanide, a chelating agent and a buffer, the composition may also include other pharmaceutically acceptable or veterinarily acceptable additives, such as carriers, diluents and excipients, anti-inflammatory agents, anti-allergic drugs and antibiotics. Suitable carriers, diluents and excipients include, where appropriate, solvents, dispersion agents, preservatives, penetration agents, surfactants, viscosity adjusters, isotonic and absorption agents and the like. Some solvents, such as various alcohols (eg. benzyl alcohol), should not be topically administered to the ear canal due to the irritant effect on a sensitive tympanum and/or canal denuded of its protective lining.

In a preferred embodiment, the composition includes a non-ionic, cationic or amphoteric surfactant or a combination thereof. Suitable surfactants include, but are not limited to, polysorbates, alkoxyphenol ethoxylates, poloxamines and betaines. Preferred surfactants are nonoxynol, octoxynol phospholipids, polysorbate 20, polysorbate 80 and cocamidopropyl betaine. The surfactant will generally be present at a concentration of 0.0001% w/w (1 ppm) to 5% w/w of the composition, preferably 0.001 to 2% w/w, most preferably 0.01 to 2% w/w, especially about 0.2% w/w. In some embodiments, the preferred amount of surfactant is in the range of 0.01 to 0.02% w/w of the composition, especially about 0.015% w/w of the composition.

Suitable agents that enhance penetration into exudates and waxes or through the epithelial lining (epidermis and dermis) include, but are not limited to, dimethyl sulfoxide, polyvinyl pyrrolidone and light oils such as isopropyl myristate. Light oils also dissolve the oily waxes produced by ears and this is a valuable effect.

Suitable anti-inflammatory agents include, but are not limited to, corticosteroids such as prednisolone, triamcinolone, dexamethasone, betamethasone and momethasone, non-steroidal anti-inflammatory drugs such as, but not limited to, ibuprofen, ketoprofen, suprofen, caprofen, meloxicam, tolfenamic acid, piroxicam, firocoxib and ketorolac. Suitable anti-allergic drugs include, but not limited to, cromolyn, emedastine, olopatadine and cyclosporine.

Suitable viscosity enhancers include, but are not limited to, propylene glycol, polyethylene glycol, polypropylene glycol(s), bentonite, celluloses such as methylcellulose, ethylcellulose and carboxymethylcellulose, and tragacanth.

Suitable antibiotics include, but are not limited to, fluoroquinolones such as ciprofloxacin, norfloxacin, ofloxacin, enoxacin, perfloxacin, fleroxacin, enrofloxacin, marbofloxacin, sarafloxacin, orbifloxacin, danofloxacin; aminoglycosides such as streptomycin, netilmicin, kanamycin, neomycin, tobramycin, amikacin, sisomicin, ribostamycin, dibekacin, framycetin, gentamycin, penicillins and aminopenicillins such as penicillin, ampicillin, amoxicillin, nafcillin, oxacillin and ticarcillin, cephalosporins such as ceftriaxone, cephalexin, cefadroxil and ceftiofur, β-lactams such as clavulanic acid which may be used in conjunction with penicillins or aminopenicillins, macrolides such as clarythromycin and erythromycin and other antibiotics such as dactinomycin, clindamycin, naladixic acid, chloramphenicol, rifamopin, clofazimine, spectinomycin, polymyxin B, colistin, minocycline, vancomycin, hygromycin B or C, fusidic acid, trimethoprim and cefotaxim.

The composition may optionally include a preservative. Many preservatives and mixtures thereof are known to those skilled in the art. Suitable preservatives which may be incorporated in the composition include, but are not limited to, sodium benzoate, alpha-tocopherol, ascorbic acid, sorbic acid, benzoic acid, methyl paraben, ethyl paraben, propyl paraben, butyl paraben or sodium bisulfate. In some embodiments the preservative is methyl paraben, propyl paraben or mixtures thereof.

In a preferred embodiment of the invention there is provided a method of treating or preventing infections of the external ear of a dog comprising topical administration of an effective amount of an aqueous composition comprising:
  (i) a chelating agent,
  (ii) a buffering agent, and
  (iii) at least one bis(biguanide) or polymeric biguanide or a mixture thereof, or pharmaceutically acceptable salts thereof,
to the external ear of the dog.

According to a further embodiment, there is provided a use of
  (i) water,
  (ii) a chelating agent,
  (iii) a buffering agent, and
  (iv) at least one bis(biguanide) or polymeric biguanide or a mixture thereof, or pharmaceutically acceptable salts thereof,
in the manufacture of a medicament for the treatment of an infection in the external ear of a dog.

The ear canal of the modern dog is long and convoluted and is therefore not self-cleaning. Dogs are unable to keep their ears sufficiently clean to prevent infection. Dogs that are particularly susceptible to ear infection tend to have long hair and pendulous ears.

A further difficulty with treating ear infections in dogs is that once drops or liquid has been placed in the ear canals, it is a reflex to shake their head to remove the liquid. It is important to have an ear wash or composition that will act rapidly upon administration to the ear canal.

In another preferred embodiment there is provided a veterinary ear wash composition comprising:
  (i) water,
  (ii) a chelating agent,
  (iii) a buffering agent, and
  (iv) at least one bis(biguanide) or polymeric biguanide or a mixture thereof, or pharmaceutically acceptable salts thereof;
with the proviso that component (iv) is not chlorhexidine.

Preferably the polymeric biguanide is PHMB, the chelating agent is disodium or tetrasodium EDTA and the buffering agent is Tris.

In yet another preferred embodiment, there is provided a veterinary ear wash composition comprising:
  (i) water,
  (ii) a chelating agent,
  (iii) a buffering agent,
  (iv) at least one bis(biguanide) or polymeric biguanide or a mixture thereof, or pharmaceutically acceptable salts thereof, and
  (v) preservative;
wherein component (iv) is present at a concentration in the range of greater than 0.02% to 0.5% w/w of the composition.

Figure 1:
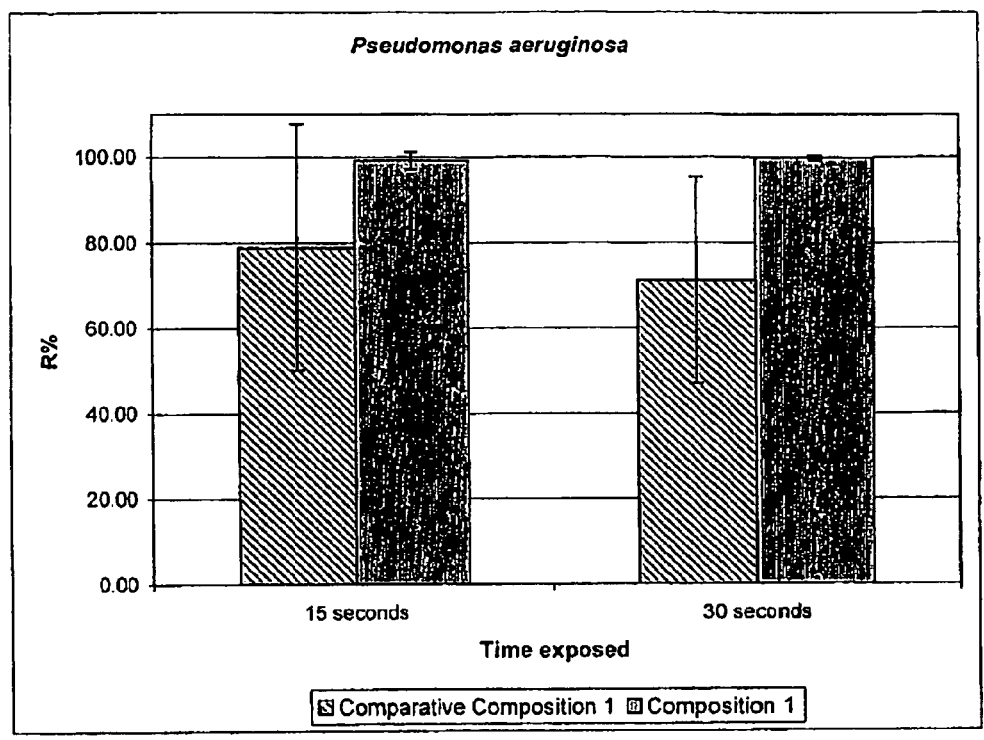
FIG. 1 is a graphical representation of the average reduction in *Pseudomonas aeruginosa* numbers (R %) for a polyhexinide/Tris/EDTA composition compared with a Tris/EDTA composition at 15 and 30 seconds exposure times.

Those skilled in the art will appreciate that the invention described herein is susceptible to variations and modifications other than those specifically described. It is to be understood that the invention includes all such variations and modifications which fall within the spirit and scope.

The invention will now be described with reference to the following examples which are included for the purpose of illustration only and are not intended to limit the generality of the invention hereinbefore described.

EXAMPLES

Composition 1

| Component | g/L |
|---|---|
| Tris | 6.05 |
| Disodium EDTA | 1.20 |
| Cosmocil CQ ™ | 1.0 |
| Propylene Glycol | 20.0 |
| Polysorbate 20 | 2.0 |

-continued

| Component | g/L |
| --- | --- |
| Phosphoric acid | to pH 8.0 |
| Purified water | to 1 L |

Add Tris, disodium-EDTA, cosmocil CQ™, polysorbate 20 and propylene glycol to approximately 750 g of purified water and stir until dissolved. Adjust to pH 8.0 with phosphoric acid. Add the balance of purified water to final mass of 1 L.

Composition 2

| Component | g/L |
| --- | --- |
| Tris | 6.05 |
| Disodium EDTA | 1.20 |
| Cosmocil CQ ™ | 1.0 |
| Polysorbate 20 | 2.0 |
| Phosphoric acid | to pH 8.0 |
| Purified water | to 1 L |

Add Tris, disodium-EDTA, cosmocil CQ™, polysorbate 20 to approximately 750 g of purified water and stir until dissolved. Adjust to pH 8.0 with phosphoric acid. Add the balance of purified water to final mass of 1 L.

Composition 3

| Component | mg |
| --- | --- |
| Tris | 300 |
| Disodium EDTA | 125 |
| Chlorhexidine gluconate (as 20% solution) | 135 |
| Purified water | to 250 g |

Add Tris, disodium-EDTA, chlorhexidine gluconate to approximately 200 g of purified water and stir until dissolved. Add the balance of purified water to final mass of 250 g. Final pH of 8.7.

Compositions 4-8

| g/L | Composition 4 | Composition 5 | Composition 6 | Composition 7 | Composition 8 |
| --- | --- | --- | --- | --- | --- |
| Tris | 6.05 | — | — | — | — |
| Bis-Tris | — | 10.5 | — | — | — |
| BTP | — | — | 14.1 | — | — |
| AMPD | — | — | — | 5.3 | — |
| AMP | — | — | — | — | 4.5 |
| Disodium edetate | 1.2 | 1.2 | 1.2 | 1.2 | 1.2 |
| Hydrochloric acid (concentrated) | to pH 6.7 | to pH 7.0 | to pH 6.9 | to pH 6.8 | to pH 6.8 |
| Methyl paraben | 1.0 | 1.0 | 1.0 | 1.0 | 1.0 |
| Propyl paraben | 0.3 | 0.3 | 0.3 | 0.3 | 0.3 |
| Propylene glycol | 50 | 50 | 50 | 50 | 50 |
| Cocamidopropyl betaine 30% | 0.5 | 0.5 | 0.5 | 0.5 | 0.5 |
| Cosmocil CQ | 10 | 10 | 10 | 10 | 10 |
| Purified water | to 1 L | to 1 L | to 1 L | to 1 L | to 1 L |

Dissolve buffering agents and disodium edetate in purified water. Adjust pH to around neutral with hydrochloric acid. Dissolve parabens in propylene glycol and add to bulk. Add cocamidopropyl betaine. Add Cosmocil CQ. Add water to volume and check pH.

Comparative Composition 1 (Purchased as Dermapet TrizEDTA)

| Component | mg |
| --- | --- |
| Tris | 533 |
| Disodium EDTA | 141 |
| trisHCl | 176 |
| Purified water | to 112 mL |

Tris, Disodium EDTA and trisHCl were mixed and ground. The ground mixture was added to a bottle and 112 mL of water added. Bottle was shaken for 10 seconds to dissolve and then left to sit for 2 hours. The pH was between 7.9 and 8.1.

Comparative Composition 2 (Purchased as DVM Pharmaceuticals T8 Solution™)

| Component | g/L |
| --- | --- |
| Tris | 4.7 |
| Tris HCl | 4.3 |
| tetrasodium EDTA | 1.3 |
| Nonoxynol 12 | 5.0 |
| PPG 12/PEG 50 | 5.0 |
| Benzyl alcohol | 12.0 |
| Purified water | up to 1 L. |

Tetrasodium EDTA, Tris, Tris HCl, benzyl alcohol, nonoxynol 12, and polypropylene glycol 12 (PPG 12) and polyethylene glycol 50 (PEG 50) were added stepwise to a beaker of water with stirring. The pH was adjusted to 8.5 and the volume made up to 1 L with water.

Example 1

Twelve *Pseudomonas aeruginosa* bacteria isolates were obtained from University and commercial laboratories which receive samples from clinical cases. The isolates were selected for maximum resistance to the usual antibiotics available in clinical practice.

Four milliliters of two Tris EDTA formulations, Composition 1 and Comparative Composition 1, were challenged with a 1 mL inoculum containing (on average) $10^8$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 24 hours.

Results are expressed as % R. The R %=100(1−Ta/Cax Cb/Tb) where R=reduction in microbe numbers due to treatment. Ta=mean count in the treatment group after treatment. Tb=Mean count in the treatment group before treatment. Ca=mean count in the control group after treatment. Cb=Mean count in the control group before treatment from materials and methods.

The results are shown in FIG. 1. FIG. 1 shows a significant and rapid reduction in microbe numbers when the micro-organisms are exposed to Composition 1 comprising Tris, EDTA and polyhexanide, as compared to exposure with Comparative Composition 1 which is a Tris/EDTA product.

Example 2

Five *Staphylococcus intermedius* bacteria isolates were obtained from University and commercial laboratories which receive samples from clinical cases.

Four milliliters of two Tris EDTA formulations, Composition 1 and Comparative Composition 1, were challenged with a 1 mL inoculum containing (on average) $10^8$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 24 hours.

Results are expressed as % R, as outlined in Example 1 above.

Figure 2:
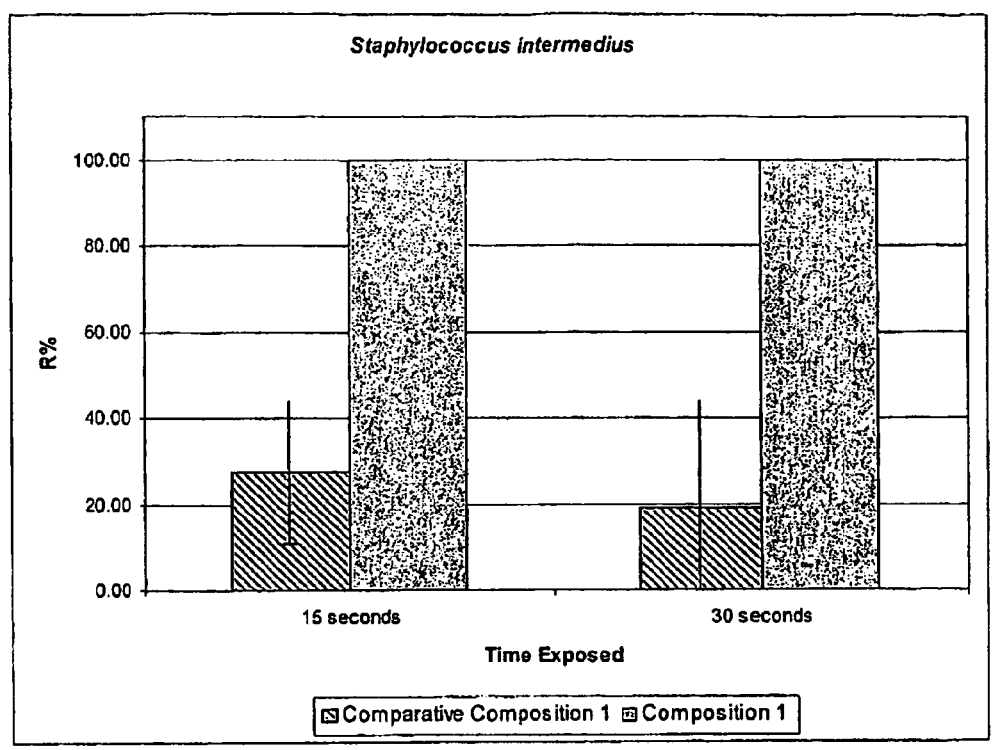
FIG. 2 is a graphical representation of the average reduction in *Staphylococcus intermedius* numbers (R %) for a polyhexinide/Tris/EDTA composition compared with a Tris/EDTA composition at 15 and 30 seconds exposure times.

The results are shown in FIG. 2.

FIG. 2 shows a significant and rapid reduction in microbe numbers when the micro-organisms are exposed to Composition 1 comprising Tris, EDTA and polyhexanide, as compared to exposure with Comparative Composition 1 which is a Tris/EDTA product.

Example 3

A *Malassezia pachydermatis* yeast isolate was obtained from a commercial laboratory which receives samples from clinical cases.

Four milliliters of two Tris EDTA formulations, Composition 1 and Comparative Composition 1, were challenged with a 1 mL inoculum containing (on average) $10^5$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 48-72 hours.

Results are expressed as % R, as described in Example 1.

Figure 3:
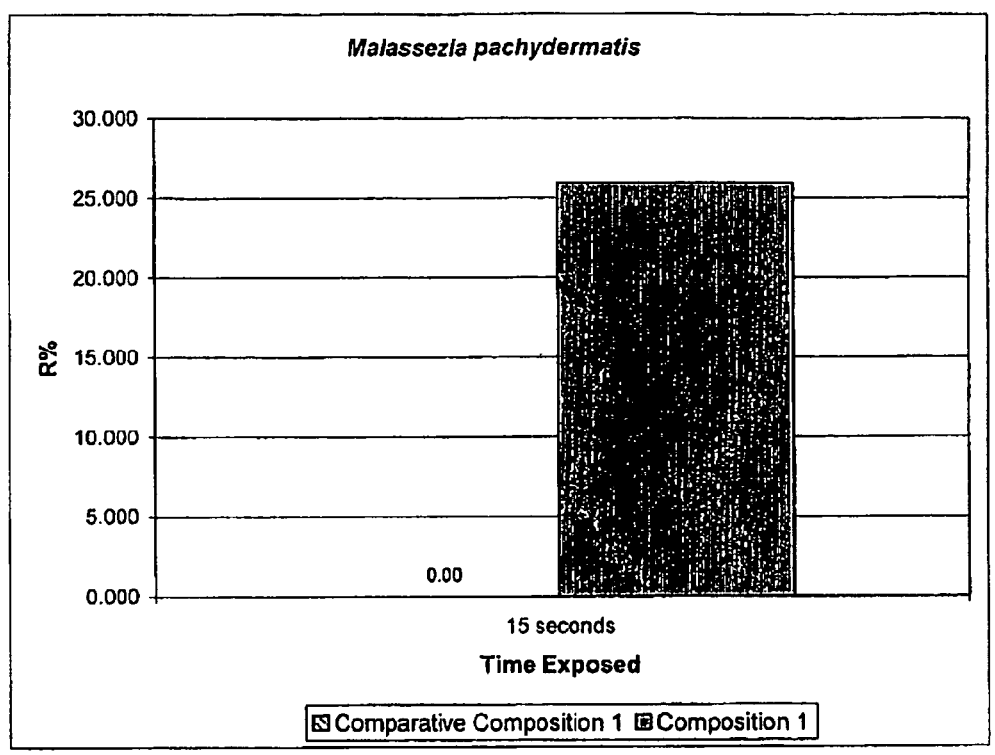
FIG. 3 is a graphical representation of the average reduction in *Malassezia pachydermatis* numbers (R %) for a polyhexinide/Tris/EDTA composition compared with a Tris/EDTA composition at 15 seconds exposure time.

The results are shown in FIG. 3.

FIG. 3 shows a significant and rapid reduction in yeast numbers when the micro-organisms are exposed to Composition 1 comprising Tris, EDTA and polyhexanide, as compared to exposure with Comparative Composition 1 which is a Tris/EDTA product.

Example 4

Organisms surviving from Example 1 above were then tested for antimicrobial susceptibility by the Kirby-Bauer Disc Diffusion Method according to the National Committee for Clinical Standard (NCC 1990 MA-A4). The Antibiotic Sensitivity Discs: Ciprofloxacin (CIP), Amikacin (AK), Neomycin (N), Enrofloxacin (ENR), Polymyxin B (PB), Chloramphenicol (C), Gentamicin (GN), Clavulox (AMC), Ticarcillin (TIC), Framycetin (FY), Trimethoprim (SXT), and Cefotaxim (CTX).

The antimicrobial susceptibility test is expressed in accordance with Kirby-Bauer Disc Diffusion Method is the standardised method by the National Committee for Clinical Laboratory Standards (NCCLS, 1990, MA-A4). The % of isolates that change from resistant to a more susceptible state was expressed.

Figure 4:
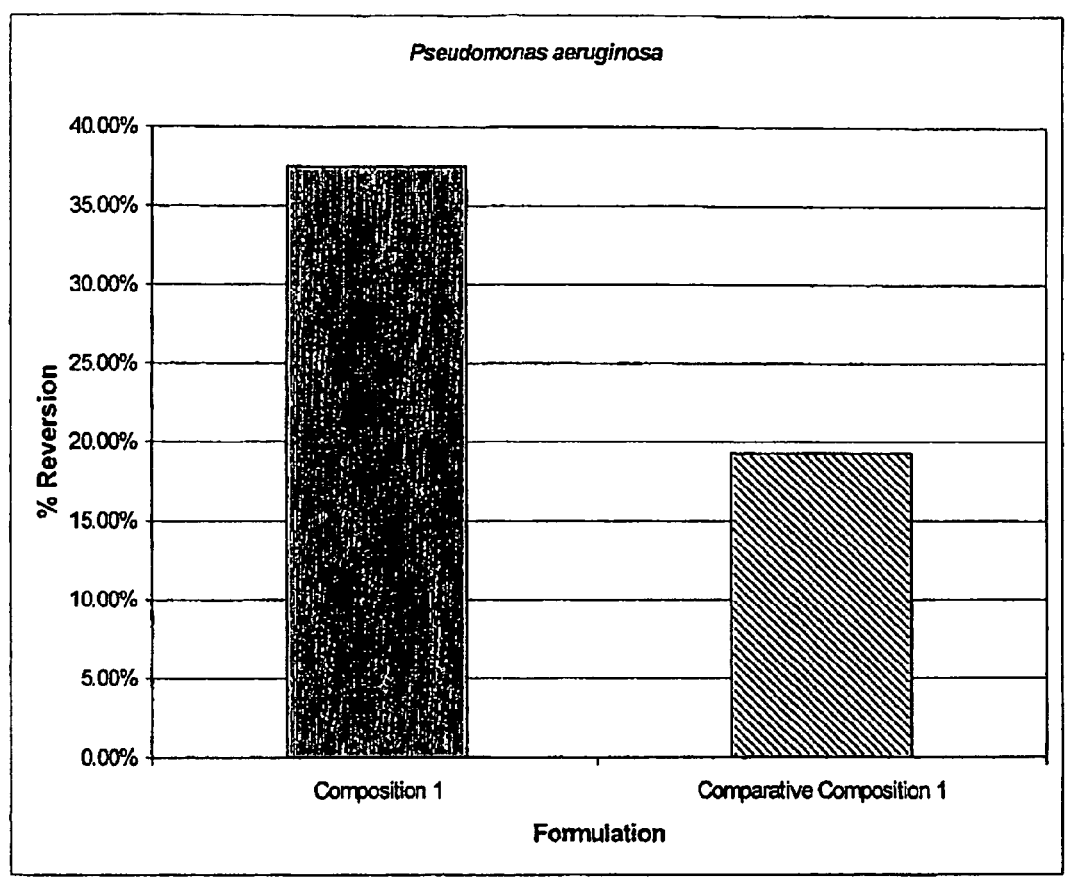
FIG. 4 is a graphical representation of the in vitro antibiotic susceptibility reversion for *Pseudomonas aeruginosa* exposed to an ear wash formulation containing polyhexinide/Tris/EDTA composition compared with a Tris/EDTA composition.

The results are shown in FIG. 4 and indicate that there was a significant increase in micro-organism sensitivity to antibiotics after treatment with Composition 1 as compared to the sensitivity of the micro-organisms treated with Comparative Composition 1.

Example 5

Ten canine patients with resistant *Pseudomonas otitis externa* that had failed conventional treatments were either pre-treated with Composition 1 or Comparative Composition 1. Culture samples were obtained for antibiotic sensitivity testing before and after flushing the ear canal with either solution. The ears were then treated again with conventional medication similar to that used in Example 4.

Figure 5:
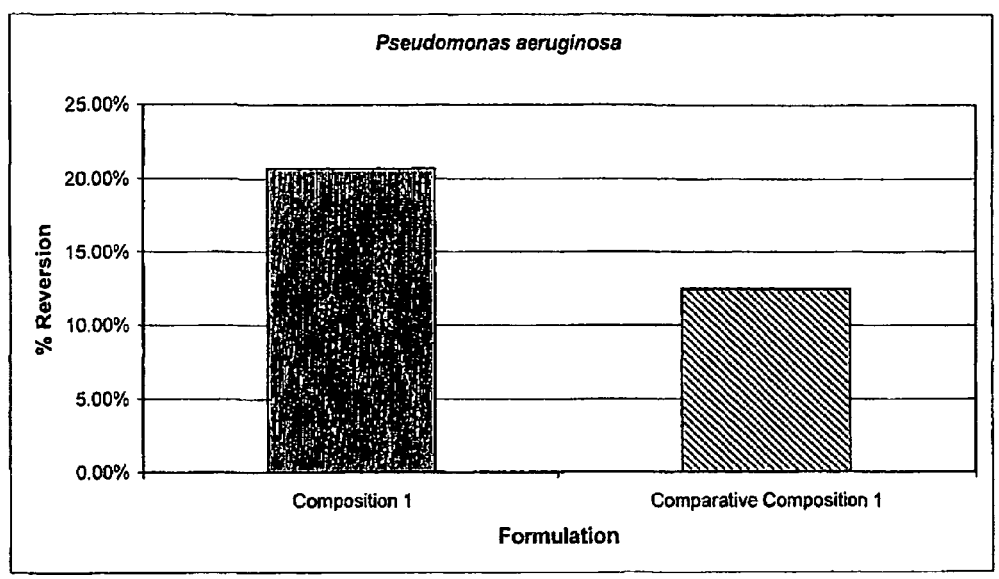
FIG. 5 is a graphical representation of the in vivo antibiotic susceptibility reversion for *Pseudomonas aureginosa*. exposed to an ear wash formulation containing polyhexinide/Tris/EDTA composition compared with a Tris/EDTA composition.

The results are shown in FIG. 5 and indicate that there was a significant increase in susceptibility of the *Pseudomonas* micro-organism infecting the dogs ears when they were treated with Composition 1 compared to the sensitivity of the micro-organisms infecting the ears of dogs treated with Comparative Composition 1. No adverse effects or ototoxicity were observed when the dogs were treated with Composition 1.

Example 6

Four *Pseudomonas aeruginosa* bacteria isolates were obtained from University and commercial laboratories which receive samples from clinical cases. The isolates were selected for maximum resistance to the usual antibiotics available in clinical practice.

Four milliliters of three Tris EDTA formulations, Composition 4, Comparative Composition 1 and Comparative Composition 2, were challenged with a 1 mL inoculum containing (on average) $10^8$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 24 hours.

Results are expressed as % R as outlined in Example 1.

The results are shown in Table 1. Table 1 shows a significant and rapid reduction in microbe numbers when the micro-organisms are exposed to Composition 4, comprising Tris, EDTA and polyhexanide as compared to the Comparative Compositions which are Tris/EDTA products.

TABLE 1

| | *Pseudomonas aeruginosa* | | |
|---|---|---|---|
| % R | Composition 4 | Comparative Composition 1 | Comparative Composition 2 |
| 15 seconds | 99.95 | 47.21 | 89.55 |
| 30 seconds | 99.95 | 38.73 | 91.58 |

Example 7

Two *Staphylococcus intermedius* bacteria isolates were obtained from University and commercial laboratories which receive samples from clinical cases.

Four milliliters of three Tris EDTA formulations, Composition 4, Comparative Composition 1 and Comparative Composition 2, were challenged with a 1 mL inoculum containing (on average) $10^8$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 24 hours.

Results are expressed as % R, as outlined in Example 1 above.

The results are shown in Table 2. Table 2 shows a significant and rapid reduction in microbe numbers when the micro-organisms are exposed to Composition 4, comprising Tris, EDTA and polyhexanide as compared to exposure with Comparative Composition 1 or 2 which are Tris/EDTA products.

TABLE 2

| | Staphylococcus intermedius | | |
|---|---|---|---|
| % R | Composition 4 | Comparative Composition 1 | Comparative Composition 2 |
| 15 seconds | 100.00 | 14.87 | 16.58 |
| 30 seconds | 100.00 | 9.03 | 31.08 |

Example 8

Two *Pseudomonas aeruginosa* bacteria isolates were obtained from University and commercial laboratories which receive samples from clinical cases. The isolates were selected for maximum resistance to the usual antibiotics available in clinical practice.

Four milliliters of five Tris EDTA formulations, Composition 4, Composition 5, Composition 6, Composition 7, and Composition 8, were challenged with a 1 mL inoculum containing (on average) $10^8$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 24 hours.

Results are expressed as % R as outlined in Example 1.

The results are shown in Table 3. Table 3 shows no difference in the reduction in microbe numbers when the micro-organisms are exposed to compositions comprising EDTA and polyhexanide and including a range of aminoalcohol or aminopolyol buffers.

TABLE 3

| Pseudomonas aeruginosa | | |
|---|---|---|
| | % R 15 seconds | % R 30 seconds |
| Composition 4 | 99.91 | 99.90 |
| Composition 5 | 99.90 | 99.97 |
| Composition 6 | 99.91 | 99.98 |
| Composition 7 | 100.00 | 99.97 |
| Composition 8 | 99.99 | 100.00 |

Example 9

Two *Proteus* spp. bacteria isolates were obtained from University and commercial laboratories which receive samples from clinical cases.

Four milliliters of three Tris EDTA formulations, Composition 4, Comparative Composition 1 and Comparative Composition 2, were challenged with a 1 mL inoculum containing (on average) $10^8$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 24 hours.

Results are expressed as % R, as outlined in Example 1 above.

The results are shown in Table 4. Table 4 shows a significant and rapid reduction in microbe numbers when the micro-organisms are exposed to Composition 4, comprising Tris, EDTA and polyhexanide as compared to exposure with Comparative Compositions 1 or 2 which are Tris/EDTA products.

TABLE 4

| | Proteus spp. | | |
|---|---|---|---|
| % R | Composition 4 | Comparative Composition 1 | Comparative Composition 2 |
| 15 seconds | 33.41 | 14.12 | 21.39 |
| 30 seconds | 46.82 | 20.67 | 16.68 |

Example 10

Two *Escherichia coli* bacteria isolates were obtained from University and commercial laboratories which receive samples from clinical cases.

Four milliliters of three Tris EDTA formulations, Composition 4, Comparative Composition 1 and Comparative Composition 2, were challenged with a 1 mL inoculum containing (on average) $10^8$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 24 hours.

Results are expressed as % R, as outlined in Example 1 above.

The results are shown in Table 5. Table 5 shows a significant and rapid reduction in microbe numbers when the micro-organisms are exposed to Composition 4, comprising Tris, EDTA and polyhexanide as compared to exposure with Comparative Compositions 1 or 2 which are Tris/EDTA products.

TABLE 5

| | Escherichia coli | | |
|---|---|---|---|
| % R | Composition 4 | Comparative Composition 1 | Comparative Composition 2 |
| 15 seconds | 100.00 | 19.81 | 34.23 |
| 30 seconds | 100.00 | 13.90 | 4.83 |

Example 11

Two *Malassezia pachydermatis* yeast isolates where obtained from a commercial laboratory which receives samples from clinical cases.

Four milliliters of three Tris EDTA formulations, Composition 4, Comparative Composition 1 and Comparative Composition 2, were challenged with a 1 mL inoculum containing (on average) $10^5$ colony-forming units (CFU) per mL organisms for a specific graded and varying time. The live count (by dilution in PBS Buffer with lecithin in CFU) after the time treatment was calculated by subculturing a specified volume onto growth media and cultured in a 37° C. incubator over 48-72 hours.

Results are expressed as % R, as described in Example 1.

The results are shown in Table 6. Table 6 shows a significant and rapid reduction in yeast numbers when the micro-organisms are exposed to Composition 4 comprising Tris, EDTA and polyhexanide as compared to exposure with Comparative Compositions 1 or 2 which are Tris/EDTA products.

TABLE 6

*Malassezia pachydermatis*

| % R | Composition 4 | Comparative Composition 1 | Comparative Composition 2 |
|---|---|---|---|
| 15 seconds | 99.06 | 37.07 | 0.00 |
| 30 seconds | 100.00 | 74.58 | 22.78 |

Example 12

Organisms surviving from Example 6 above were then tested for antimicrobial susceptibility by the Kirby-Bauer Disc Diffusion Method according to the National Committee for Clinical Standard (NCC 1990 MA-A4). The Antibiotic Sensitivity Discs: Amikacin (AK), Neomycin (N), Enrofloxacin (ENR), Polymyxin B (PB), Gentamicin (GN), Ticarcillin (TIC), and Framycetin (FY).

The antimicrobial susceptibility test is expressed in accordance with Kirby-Bauer Disc Diffusion Method is the standardised method by the National Committee for Clinical Laboratory Standards (NCCLS, 1990, MA-A4). The % of isolates that change from resistant to a more susceptible state was expressed.

The results are shown in Table 7 and indicate that there was a significant increase in micro-organism sensitivity to antibiotics after treatment with Composition 4 comprising Tris, EDTA and polyhexanide as compared to the sensitivity of the micro-organisms treated with Comparative Compositions 1 or 2 which are Tris/EDTA products.

TABLE 7

*Pseudomonas aeruginosa*

| | Composition 4 | Comparative Composition 1 | Comparative Composition 2 |
|---|---|---|---|
| Average % reversion | 23 | 5 | 14 |

Example 13

A tris EDTA polyhexanide composition, as described herein, Comparative Composition 1 and Comparative Composition 2 were tested for efficacy of antimicrobial preservative using BP 2003 Appendix XVI C and the results summarised in Table 8. In contrast to Comparative Compositions 1 and 2, Composition 4, the tris EDTA polyhexanide composition, meets the BP antimicrobial preservative requirements (Criteria A).

TABLE 8

Efficacy of antimicrobial preservation
Criteria of acceptance as per BP 2003 - Ear Preparations Criteria A

| Ear Flush Formulation | Inoculum/ml of formulation | 6 hour | 24 hour | 28 days |
|---|---|---|---|---|
| *Staphylococcus aureus* | | | | |
| Composition 4 | 6.18 | pass | pass | pass |
| Comparative Composition 1 | 7.94 | pass | pass | pass |
| Comparative Composition 2 | 7.94 | pass | pass | pass |
| *Pseudomonas aeruginosa* | | | | |
| Composition 4 | 5.97 | pass | pass | pass |
| Comparative Composition 1 | 5.97 | pass | pass | pass |
| Comparative Composition 2 | 5.97 | pass | pass | pass |

| Ear Flush Formulation | Inoculum/ml of formulation | 7 day | 28 days |
|---|---|---|---|
| *Candida albicans* | | | |
| Composition 4 | 6.15 | pass | pass |
| Comparative Composition 1 | 6.18 | pass | pass |
| Comparative Composition 2 | 6.18 | pass | pass |
| *Aspergillus niger* | | | |
| Composition 4 | 6.15 | pass | pass |
| Comparative Composition 1 | 5.84 | fail | fail |
| Comparative Composition 2 | 5.84 | fail | pass |

REFERENCES

Ashworth C. D. and Nelson D. R., 1990, Antimicrobial potentiation of irrigation solutions containing tris-(hydroxymethyl)aminomethane-EDTA, J. Am. Vet. Med. Assoc., 197(11), 1513-1514.

Aursnes J. 1981 a. Vestibular damage from chlorhexidine in guinea pigs. Acta Otolaryngology 92. 89-100.

Aursnes J. 1981 b. Cochlear damage from chlorhexidine in guinea pigs. Acta Otolaryngology 92. 259-271.

Block S. S., 2001 Disinfection, Sterilization and Preservation. Chapter 2 DEFINITION of TERMS in the 5th edition published by LIPINCOTT WILLIAMS & WILKINS page 19 to 31.

East G. C., McIntyre J. E., Shao J., 1997, Polymer, 38(15), 3973-3984

Facia A. M., Marfei G., Re. G., 1997, Potentiating effect of EDTA-Tris on the activity of antibiotics against resistant bacteria associated with otitis, dermatitis and cystitis, J. Small Animal Practice, 38, 243-245.

Facia A. M., Nebbia P., Re G., 1993, Potentiation of the in-vitro activity of some antimicrobial agents against selected Gram-negative bacteria by EDTA-tromethamine, Veterinary Research Communication, 17, 77-84.

Farng R. K., Mrha S., 2003, Antimicrobial wash and carrier solutions and uses thereof, WO 03/086332.

Foster A. and DeBoer D., 1998, The role of *pseudomonas* in canine ear disease, Compendium on Continuing Education, 20(8), 909-918.

Gotthelf N., 2003, evaluation of the in-vitro effects of tris-EDTA on the minimum inhibitory concentration (MIC) of enrofloxacin against ciprofloxacin resistant *Pseudomonas aureginosa*, Proceedings of the 19th Annual Congress of ESUD/ECVD, Tenerfife, 2003, p145.

Green C., 1984, The clinical use of topical buffered EDTA solutions in the treatment of Gram negative bacterial infections of dogs and cats. Antimicrobial chemotherapy in 'Clinical Microbiology of Infectious Diseases of the Cat and Dog, p171, Saunders, Philadelphia.

Harper W. E. S. and Epis J. A., 1987, Effect of Chlorhexidine/EDTA/Tris against bacterial isolates from clinical specimens, Microbios, 51, 107-112.

Harvey R. G., Harari J., Delauche A. J., 2001, Ear Diseases of the Dog and Cat, Manson Publishing, page 216.

Ikeda T., Yamaguchi H., Tazuke S., 1984, Antimicrobial Agents and Chemotherapy, 26(2), 139-144.

Izatt R. M., Pawlak K., Bradshaw J. S., 1995, Thermodynamic and Kinetic data for Macrocycle Interaction with cations, anions and neutral molecules, Chem. Rev., 95, 1261.

Kirby-Bauer disc diffusion method is the standardised method by the National Committee for Clinical Laboratory Standards (NCCLS, 1990, MA-A4) in Quinn P. J., Carter, M. E.

Merchant S. R., 1994, Ototoxicity, Veterinary Clinics of North America: Small Animal Practice, 24(5), 976.

Merchant S. R., Neer, T. M., Tedford, B. L., Twedt A. C., Cheramie P. M., Strain G. M., 1993, Ototoxicity Assessment of a chlorhexidine otic preparation in dogs, Progress in Veterinary Neurology, 4(3), 72-75.

Neer T. M., 1982, Otitis media, Compendium of continuing Education, Vol 4, p410-417 Facia A. M., Nebbia P., Re G., 1993, Veterinary Research Communication, Vol 17, 77-84.

Paterson S., 2003 New Concepts in Ear Cleaning TrizEDTA (EDTA tris) DermaPet articles of Interest. Found at: http://www.dermapet.com/articles/new_concepts.html Pearman J. W., Bailey M., Harper W. E. S., 1988, Comparison of the Efficacy of "Trisdine" and Kanamycin—Colistin Bladder Instillations in Reducing Bacteriuria during Intermittent Catheterisation of Patients with Acute Spinal Cord Trauma, British J. of Urology, 62, 140-144.

Quinn P. J., Carter M. E., Antimicrobial Agents in: Clinical Veterinary Microbiology, editors Markey B., Carter G. R., 1994, Mosby-Yearbook Europe Ltd., 95-102.

Rohn G. N., Meyerhoff W. L., Wright C. G., 1993, Ototoxicity of Topical Agents, Otolaryngology Clinics of North America, 26(5), 747-758.

Sparkes T. A., Kemp D. T., Wooley R. E., Gibbs P. S., 1994, Antimicrobial effects of combinations of EDTA-Tris and amikacin or neomycin on the microorganism associated with Otitis externa in dogs, Veterinary Research Communications, 18, 241-249.

Willoughby K., 1989. Chlorhexadine and ototoxicity in cats. Veterinary Record 124 page 547.

Wooley R. E., Jones M. S., Gilbert J. P., Shotts E. B., 1983a, In-vitro effect of combinations of anti-microbial agents and EDTA-tromethamine on certain Gram positive bacteria, American Journal of Veterinary Research, 44(11), 2167-2169.

Wooley R. E., Jones M. S., 1983b, Action of EDTA-TRIS and antimicrobial agent combinations on selected pathogenic bacteria, Veterinary Microbiology, 8, 271-280.

The claims defining the invention are as follows:

1. A method for inhibiting or treating infections of the external ear in a mammal, comprising topical administration to the external ear of an effective amount of a pharmaceutical or veterinary ear wash or ear lavage composition consisting essentially of:
   (i) a chelating agent, wherein the chelating agent is a salt of ethylene diamine tetraacetic acid (EDTA);
   (ii) a buffering agent to provide a pH in the range of 6-8; and
   (iii) at least one polymeric biguanide or mixture thereof of formula (IV):

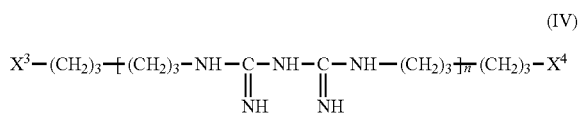

or a pharmaceutically acceptable salt or tautomer thereof, wherein n is an integer from 3 to 500 and $X^3$ and $X^4$ are independently selected from —$NH_2$, —NH—C(=NH)—NH—CN, optionally substituted alkyl, optionally substituted cycloalkyl, optionally substituted aryl, optionally substituted heterocyclyl and optionally substituted heteroaryl;

wherein the at least one polymeric biguanide or mixture thereof is present in an amount ranging from 1.0 g/L to 10.0 g/L of the composition;

and wherein the composition, when applied to the external ear of a mammal, achieves a reduction in the number of viable bacteria in the ear canal in a time period of from 15 to 30 seconds following exposure to the composition, and an increase in antibiotic sensitivity of bacteria in the external ear.

2. The method of claim 1, wherein n has an average value ranging from 3 to 15.

3. The method of claim 1, wherein the salt of EDTA is disodium EDTA, trisodium EDTA, tetrasodium EDTA, dipotassium EDTA, tripotassium EDTA, lithium EDTA, dilithium EDTA, ammonium EDTA, diammonium EDTA or calcium disodium EDTA.

4. The method of claim 1, wherein the salt of EDTA is disodium EDTA.

5. The method of claim 1, wherein the buffering agent is triethylamine, triethylenetetramine, tetraethylethylenediamine, tetramethylenediamine, N,N'-diethyl-N,N'-bis(sulfopropyl)-ethylenediamine, N,N'diethylpiperazine, piperazine-N,N'-bis(alkylsulfonic acids), (N-morpholino) alkylsulfonic acids, 2-aminoethanol, 2-amino-2methyl-1-propanol, triethanolamine, tris(hydroxymethyl) aminomethane, 2-amino-2-methyl-1,3-propanediol, bis-(2-hydroxyethyl)iminotris(hydroxymethyl)methane, 2-dimethylamino-2-methyl-1-propanol, 2-amino-2-ethyl-1,3-propanediol and 1,3-bis(tris[hydroxymethyl]methyl) aminopropane, N,N-bis(hydroxyethyl)-2-aminoethanesulfonic acid, N-[tris(hydroxymethyl)methyl]-3-aminopropanesulfonic acid, N,N-bis(2-hydroxyethyl) glycine, N,N-bis(2-hydroxyethyl)taurine, diethanolamine, triethanolamine N-tris(hydroxymethyl)methylglycine, or a pharmaceutically or veterinarily acceptable salt or mixture thereof.

6. The method of claim 1, wherein the buffering agent is tris(hydroxymethyl)aminomethane, or a pharmaceutically or veterinarily acceptable salt or mixture thereof.

7. The method of claim 1, wherein the at least one polymeric biguanide or mixture thereof is present in an amount ranging from 1 g/L to 2 g/L of the composition.

8. The method of claim 4, wherein the at least one polymeric biguanide or mixture thereof is polyhexamethylene biguanide (PHMB).

9. The method of claim 8, wherein the buffer is tris (hydroxymethyl)aminomethane.

10. The method of claim 1 wherein the composition is an aqueous composition.

11. The method of claim 1 wherein the mammal is a dog.

12. The method of claim 1 further comprising the step of administering an antibiotic to the mammal.

13. A method for inhibiting or treating infections of the external ear in a mammal, comprising topical administration to the external ear of an effective amount of a composition comprising:

(i) a chelating agent, wherein the chelating agent is a salt of ethylene diamine tetraacetic acid (EDTA);
(ii) a buffering agent to provide a pH in the range of 6-8; and
(iii) at least one polymeric biguanide or mixture thereof of formula (IV):

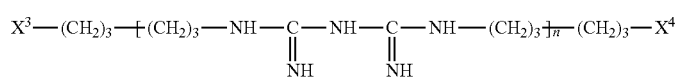

(IV)

or a pharmaceutically acceptable salt or tautomer thereof, wherein n is an integer from 3 to 500 and $X^3$ and $X^4$ are independently selected from —$NH_2$, —NH—C(=NH)—NH—CN, optionally substituted alkyl, optionally substituted cycloalkyl, optionally substituted aryl, optionally substituted heterocyclyl and optionally substituted heteroaryl; and wherein the at least one polymeric biguanide or mixture thereof is present in an amount ranging from 1.0 g/L to 10.0 g/L of the composition.

14. A method for increasing the susceptibility of bacteria in the external ear of a mammal to antibiotics, comprising administering an effective amount of a composition comprising:
(i) a chelating agent, wherein the chelating agent is a salt of ethylene diamine tetraacetic acid (EDTA);
(ii) a buffering agent to provide a pH in the range of 6-8; and
(iii) at least one polymeric biguanide or mixture thereof of formula (IV):

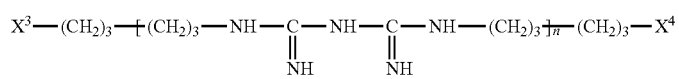

(IV)

or a pharmaceutically acceptable salt or tautomer thereof, wherein n is an integer from 3 to 500 and $X^3$ and $X^4$ are independently selected from —$NH_2$, —NH—C(=NH)—NH—CN, optionally substituted alkyl, optionally substituted cycloalkyl, optionally substituted aryl, optionally substituted heterocyclyl and optionally substituted heteroaryl; and wherein the at least one polymeric biguanide or mixture thereof is present in an amount ranging from 1.0 g/L to 10.0 g/L of the composition.

15. A method for reducing the number of viable bacteria in the external ear of a mammal in a time period of from 15 to 30 seconds following exposure to a composition comprising:
(i) a chelating agent, wherein the chelating agent is a salt of ethylene diamine tetraacetic acid (EDTA);
(ii) a buffering agent to provide a pH in the range of 6-8; and
(iii) at least one polymeric biguanide or mixture thereof of formula (IV):

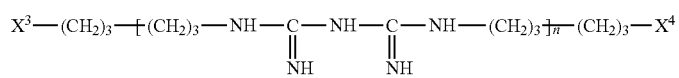

(IV)

or a pharmaceutically acceptable salt or tautomer thereof, wherein n is an integer from 3 to 500 and $X^3$ and $X^4$ are independently selected from —$NH_2$, —NH—C(=NH)—NH—CN, optionally substituted alkyl, optionally substituted cycloalkyl, optionally substituted aryl, optionally substituted heterocyclyl and optionally substituted heteroaryl; and wherein the at least one polymeric biguanide or mixture thereof is present in an amount ranging from 1.0 g/L to 10.0 g/L of the composition.

16. The method of any one of claims 13-15, wherein n has an average value ranging from 3 to 15.

17. The method of any one of claims 13-15, wherein the salt of EDTA is disodium EDTA, trisodium EDTA, tetrasodium EDTA, dipotassium EDTA, tripotassium EDTA, lithium EDTA, dilithium EDTA, ammonium EDTA, diammonium EDTA or calcium disodium EDTA.

18. The method of any one of claims 13-15, wherein the salt of EDTA is disodium EDTA.

19. The method of any one of claims 13-15, wherein the buffering agent is triethylamine, triethylenetetramine, tetraethylethylenediamine, tetramethylenediamine, N,N'-diethyl-N,N'-bis(sulfopropyl)-ethylenediamine, N,N'diethylpiperazine, piperazine-N,N'-bis(alkylsulfonic acids), (N-morpholino)alkylsulfonic acids, 2-aminoethanol, 2-amino-2methyl-1-propanol, triethanolamine, tris(hydroxymethyl)aminomethane, 2-amino-2-methyl-1,3-propanediol, bis-(2-hydroxyethyl)iminotris(hydroxymethyl)methane, 2-dimethylamino-2-methyl-1-propanol, 2-amino-2-ethyl-1,3-propanediol and 1,3-bis(tris[hydroxymethyl]methyl)aminopropane, N,N-bis(hydroxyethyl)-2-aminoethanesulfonic acid, N-[tris(hydroxymethyl)methyl]-3-aminopropanesulfonic acid, N,N-bis(2-hydroxyethyl)glycine, N,N-bis(2-hydroxyethyl)taurine, diethanolamine, triethanolamine N-tris(hydroxymethyl)methylglycine, or a pharmaceutically or veterinarily acceptable salt or mixture thereof.

20. The method of any one of claims 13-15, wherein the buffering agent is tris(hydroxymethyl)aminomethane, or a pharmaceutically or veterinarily acceptable salt or mixture thereof.

21. The method of any one of claims 13-15, wherein the at least one polymeric biguanide or mixture thereof is present in an amount ranging from 1g/L to 2g/L of the composition.

22. The method of claim 18, wherein the at least one polymeric biguanide or mixture thereof is polyhexamethylene biguanide (PHMB).

23. The method of claim 22, wherein the buffer is tris(hydroxymethyl)aminomethane.

24. The method of any one of claims 13-15, wherein the composition is an aqueous composition.

25. The method of any one of claims 13-15, wherein the mammal is a dog.

26. The method of any one of claims 13-15, further comprising the step of administering an antibiotic to the mammal.

* * * * *